US011654423B2

(12) United States Patent
Ide et al.

(10) Patent No.: US 11,654,423 B2
(45) Date of Patent: May 23, 2023

(54) CATALYST COMPOSITIONS AND THEIR USE IN AROMATIC ALKYLATION PROCESSES

(71) Applicant: ExxonMobil Chemical Patents Inc., Baytown, TX (US)

(72) Inventors: Matthew S. Ide, Doylestown, PA (US); Doron Levin, Highland Park, NJ (US); Wenyih F. Lai, Bridgewater, NJ (US); Ivy D. Johnson, Lawrenceville, NJ (US); Scott J. Weigel, Allentown, PA (US); Brett T. Loveless, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 119 days.

(21) Appl. No.: 16/479,179

(22) PCT Filed: Feb. 7, 2018

(86) PCT No.: PCT/US2018/017245
§ 371 (c)(1),
(2) Date: Jul. 18, 2019

(87) PCT Pub. No.: WO2018/160327
PCT Pub. Date: Sep. 7, 2018

(65) Prior Publication Data
US 2020/0179913 A1 Jun. 11, 2020

Related U.S. Application Data

(60) Provisional application No. 62/464,713, filed on Feb. 28, 2017.

(30) Foreign Application Priority Data

May 4, 2017 (EP) .................................. 17169516

(51) Int. Cl.
*B01J 29/80* (2006.01)
*B01J 29/18* (2006.01)
(Continued)

(52) U.S. Cl.
CPC ............... *B01J 29/80* (2013.01); *B01J 29/18* (2013.01); *B01J 29/70* (2013.01); *B01J 29/7007* (2013.01);
(Continued)

(58) Field of Classification Search
CPC ... B01J 29/80; B01J 29/70; B01J 29/18; B01J 35/10; B01J 37/00; C07C 7/13; C07C 2/66; C07C 6/12
See application file for complete search history.

(56) References Cited

U.S. PATENT DOCUMENTS 6,809,055 B2 10/2004 Overbeek et al.
7,687,423 B2 * 3/2010 Moscoso ................. C01B 39/48
502/64

(Continued)

FOREIGN PATENT DOCUMENTS

CN 104549464 A 4/2015
EP 0914310 B1 10/2003
(Continued)

OTHER PUBLICATIONS

Groen et al. (Mesoporous beta zeolite obtained by desilication, 2008, Microporous and mesoporous materials, vol. 114, pp. 93-102) (Year: 2008).*
(Continued)

*Primary Examiner* — Youngsul Jeong

(57) ABSTRACT

Catalyst composition which comprises a first zeolite having a BEA* framework type and a second zeolite having a MOR framework type and a mesopore surface area of greater than 30 m²/g is disclosed. These catalyst compositions are used (Continued)

to remove catalyst poisons from untreated feed streams having one or more impurities which cause deactivation of the downstream catalysts employed in hydrocarbon conversion processes, such as those that produce mono-alkylated aromatic compounds.

24 Claims, 7 Drawing Sheets

(51) Int. Cl.
    C07C 2/66      (2006.01)
    B01J 29/70     (2006.01)
    B01J 35/10     (2006.01)
    B01J 37/00     (2006.01)
    C07C 6/12      (2006.01)
    C07C 7/13      (2006.01)
    B01J 29/06     (2006.01)

(52) U.S. Cl.
    CPC ....... B01J 35/1004 (2013.01); B01J 35/1061 (2013.01); B01J 37/0009 (2013.01); C07C 2/66 (2013.01); C07C 6/126 (2013.01); C07C 7/13 (2013.01); B01J 2029/062 (2013.01); C07C 2529/18 (2013.01); C07C 2529/70 (2013.01); C07C 2529/80 (2013.01)

(56) References Cited

U.S. PATENT DOCUMENTS

| | | |
|---|---|---|
| 8,013,199 B2 | 9/2011 | Smith |
| 8,450,232 B2 | 5/2013 | Yeh et al. |
| 10,307,733 B2 | 6/2019 | Vincent et al. |
| 2009/0306446 A1 | 12/2009 | Clark et al. |
| 2013/0211164 A1 | 8/2013 | Vincent et al. |

FOREIGN PATENT DOCUMENTS

| | | | |
|---|---|---|---|
| EP | 2041242 B1 | 3/2017 | |
| WO | 03/049857 A1 | 6/2003 | |
| WO | WO-03049857 A1 * | 6/2003 | ............ B01J 29/80 |
| WO | 2011/112189 A | 9/2011 | |
| WO | WO-2011112189 A1 * | 9/2011 | ............ B01J 29/18 |
| WO | 2017/213749 A1 | 12/2017 | |

OTHER PUBLICATIONS

Groen et al. (Alkaline-mediated mesoporous mordenite zeolites for acid-catalyzed conversions, 2007, Journal of catalysis, vol. 251, pp. 21-27) (Year: 2007).*

Kostrab, G., et al. "Tert-Butylation of toluene with Isobutylene over zeolite catalysts: Influence ofwater", Applied Catalysis A: General, Elsevier, Amsterdam, NL, vol. 323, pp. 210-218, 2007.

John, P.T. et al "Determination of mesopore surface area in presence of micropores", Carbon, Elsiever, Oxford, GB, vol. 20 No. 1, pp. 67-70, 1982.

Van Laak, A. N.C., et al., "Mesoporous mordernites obtained by sequential acid and alkaline treatments—Catalysts for cumene production with enhanced accessibility" Journal of Catalysis, Academic Press, Duluth, MN, US, vol. 276, No. 1, pp. 170-180, 2010.

* cited by examiner

CATALYST COMPOSITIONS AND THEIR USE IN AROMATIC ALKYLATION PROCESSES

CROSS REFERENCE TO RELATED APPLICATIONS

This application is a National Phase Application of PCT Application Serial No. PCT/US2018/017245, filed Feb. 7, 2018, which claims priority to and the benefit of U.S. Provisional Application No. 62/464,713, filed Feb. 28, 2017, and EP 17169516.6 which was filed May 4, 2017, the disclosures of which are incorporated herein by their reference.

FIELD OF THE INVENTION

This invention relates to catalyst compositions having an increased capacity to adsorb catalyst poisons from hydrocarbon streams. This invention also relates to the use of the catalyst compositions to remove such catalyst poisons from untreated feed streams having one or more impurities which cause deactivation of the downstream catalysts employed in hydrocarbon conversion processes, such as those that produce mono-alkylated aromatic compounds. As a result, the cycle length of such catalyst is increased.

BACKGROUND OF THE INVENTION

In a typical aromatic alkylation process, an aromatic compound is reacted with an alkylating agent, such as an olefin, in the presence of acid catalyst. For example, benzene can be reacted with ethylene or propylene to produce ethylbenzene or cumene, both of which are important intermediates in the chemical industry. In the past, commercial aromatic alkylation processes normally used $AlCl_3$ or $BF_3$ as the acid catalyst, but more recently these materials have been replaced by molecular sieve-based catalysts.

Aromatics alkylation processes employing molecular sieve-based catalysts may be conducted in either the vapor phase or the liquid phase. However, in view of the improved selectivity and decreased capital and operating costs associated with liquid phase operation, most commercial alkylation processes now operate under at least partial liquid phase conditions. Unfortunately, one disadvantage of operating under liquid phase conditions is that the molecular sieve-based catalysts tend to be more sensitive to the presence of catalyst poisons in the feed streams, especially those with a compound having at least one of the following elements: nitrogen, halogens, oxygen, sulfur, arsenic, selenium, tellurium, phosphorus, and Group 1 through Group 12 metals. Such impurities reduce the acid activity of such molecular sieve-based catalyst and hence decrease the cycle time between required regenerations of such catalyst.

The use of guard beds to remove trace contaminants from hydrocarbon feed streams is well known in the art. This is especially true for petrochemical and specialty chemical operations where product purity is critical. Normally, guard bed materials that contain bentonite clay, kaolin clay, special activated aluminas or molecular sieves are used and are placed upstream of a reaction vessel containing an acidic molecular sieve-based catalyst. These guard bed materials trap impurities in the feed streams so that product purity specifications can be met and poisoning of such catalyst can be reduced. However, such guard bed materials have limited capacity to adsorb impurities from aromatic feed streams to the low levels required for use in liquid phase alkylation processes which employ acidic molecular sieve-based catalysts. Therefore, a need exists for a guard bed material with an increased capacity to adsorb impurities more effectively. It is desirable to remove such impurities from the feed streams to such aromatic alkylation processes and thereby reduce the deactivation of the downstream acidic molecular sieve-based catalyst used in alkylation and/or transalkylation reactions.

SUMMARY OF THE INVENTION

It has now been found that the catalyst compositions of this invention have an improved capacity to adsorb catalyst poisons from hydrocarbon streams, particularly feed streams to processess to produce mono-alkylated aromatic compounds, such as benzene and ethylene, using zeolite-based alkylation catalysts, thereby increasing the cycle length of such alkylation catalysts.

In a first aspect, this invention is a catalyst composition comprising a first zeolite having a BEA* framework type and a second zeolite having a MOR framework type. The first zeolite can be zeolite beta. The second zeolite can be any one of TEA-mordenite, EMM-34, UZM-14 or combinations of two or more thereof. Also, the second zeolite can be a natural mordenite or mordenite synthesized with sodium (Na) only, (Na) Mordenite.

EMM-34 has a mesopore surface area of greater than 30 $m^2/g$ and comprising agglomerates composed of primary crystallites, wherein the primary crystallites have an average primary crystal size as measured by TEM of less than 80 nm, an aspect ratio of less than 2 and a total surface area of greater than 500 $m^2/g$. In some embodiments, EMM-34 has a ratio of the mesopore surface area to the total surface area of greater than 0.05, and is synthesized from TEA or MTEA.

The ratio of the first zeolite to the second zeolite of the catalyst composition is in the range of 90:10 to 50:50 by weight of the catalyst composition. The Si/$Al_2$ molar ratio of the second zeolite of the catalyst composition is in the range of 10 to 60. The collidine uptake of the catalyst composition can be in the range of 550 µmoles/g to 1500 µmoles/g, or in the range of 550 µmoles/g to 700 µmoles/g.

The catalyst composition of this invention can be made by a method such that the first zeolite and the second zeolite are co-crystallized in the same synthesis mixture. The catalyst composition can be made by a method such that the first zeolite and the second zeolite are co-extruded.

In a second aspect, this invention is a method for removing impurities from a hydrocarbon stream. The method comprises step (a) of supplying a feed stream and a guard bed catalyst. The feed stream comprises one or more hydrocarbons and undesirable impurities. The impurities comprise at least one compound having at least one of the following elements: nitrogen, halogens, oxygen, sulfur, arsenic, selenium, tellurium, phosphorus, and Group 1 through Group 12 metals. The guard bed catalyst comprises any one of the catalyst composition of this invention, described herein. In step (b) of the method, at least a portion of the feed stream is contacted with the guard bed catalyst to remove at least a portion of the impurities and produce a treated feed stream having a reduced amount of impurities. In one or more embodiments, the feed stream and the guard bed are supplied to a guard bed for contacting therein.

In a third aspect, this invention is a process for producing a mono-alkylated aromatic compound. The process comprises step (a) of providing a guard bed having a guard bed catalyst disposed therein. The guard bed catalyst comprises any one of the catalyst compositions of this invention. In step (b), at least a portion of an untreated feed stream is supplied to the guard bed. The untreated feed stream comprises an alkylatable aromatic compound and undesirable impurities, as defined herein. In step (c), the portion of the untreated feed stream of step (b) is contacted with the guard bed catalyst to remove at least a portion of the impurities and produce a treated feed stream having a reduced amount of impurities. In step (d), at least a portion of the treated feed stream of step (b) and an alkylating agent stream is contacted with an alkylation catalyst which is the same or different from the guard bed catalyst under suitable at least partially liquid phase reaction conditions to alkylate at least a portion of the alkylatable aromatic compound with the alkylating agent stream to produce an effluent stream. The effluent stream comprises the mono-alkylated aromatic compound and poly-alkylated aromatic compounds.

In one or more embodiments, the alkylation catalyst comprises an acidic aluminosilicate. The aluminosilicate can or is any one of a MCM-22 family molecular sieve, faujasite, mordenite, zeolite beta, or combinations of two or more thereof.

In one or more embodiments, the process further comprises one or more separation steps to recover a mono-alkylated aromatic compound stream and a poly-alkylated aromatic compounds stream.

In one or more embodiments, the process further comprises a transalkylation step of contacting the poly-alkylated aromatic compound stream and another portion of the feed stream of step (a) with a transalkylation catalyst under suitable at least partially liquid phase transalkylation conditions to transalkylate the poly-alkylated aromatic compound stream with the alkylatable aromatic compound and produce additional the mono-alkylated aromatic compound. In one or more embodiments, the transalkylation catalyst is a large pore molecular sieve having a Constraint Index of less than 2. In other embodiments, the transalkylation catalyst is a MCM-22 family material. In one or more embodiments, the portion of the feed stream of step (a) for transalkylation is first contacted with a guard bed catalyst of this invention to remove at least of a portion of impurities.

When the alkylatable aromatic compound is benzene and the alkylating agent is ethylene, the mono-alkylated aromatic compound is ethylbenzene and the poly-alkylated aromatic compound is poly-ethylbenzene. When the alkylatable aromatic compound is benzene and the alkylating agent is propylene, the mono-alkylated aromatic compound is cumene and the poly-alkylated aromatic compound is poly-isopropylbenzene.

In one or more embodiments of the process, step (b) further includes supplying an alkylating agent stream to the guard bed in addition to the feed stream which comprises the alkylatable aromatic compound and undesirable impurities. In one or more embodiments, step (c) further includes contacting the alkylating agent stream with the alkylatable aromatic compound in the presence of the guard bed catalyst to produce additional mono-alkylated aromatic compound. When operated as such, the guard bed is referred to as a reactive guard bed.

DETAILED DESCRIPTION OF THE INVENTION

Figure 1:
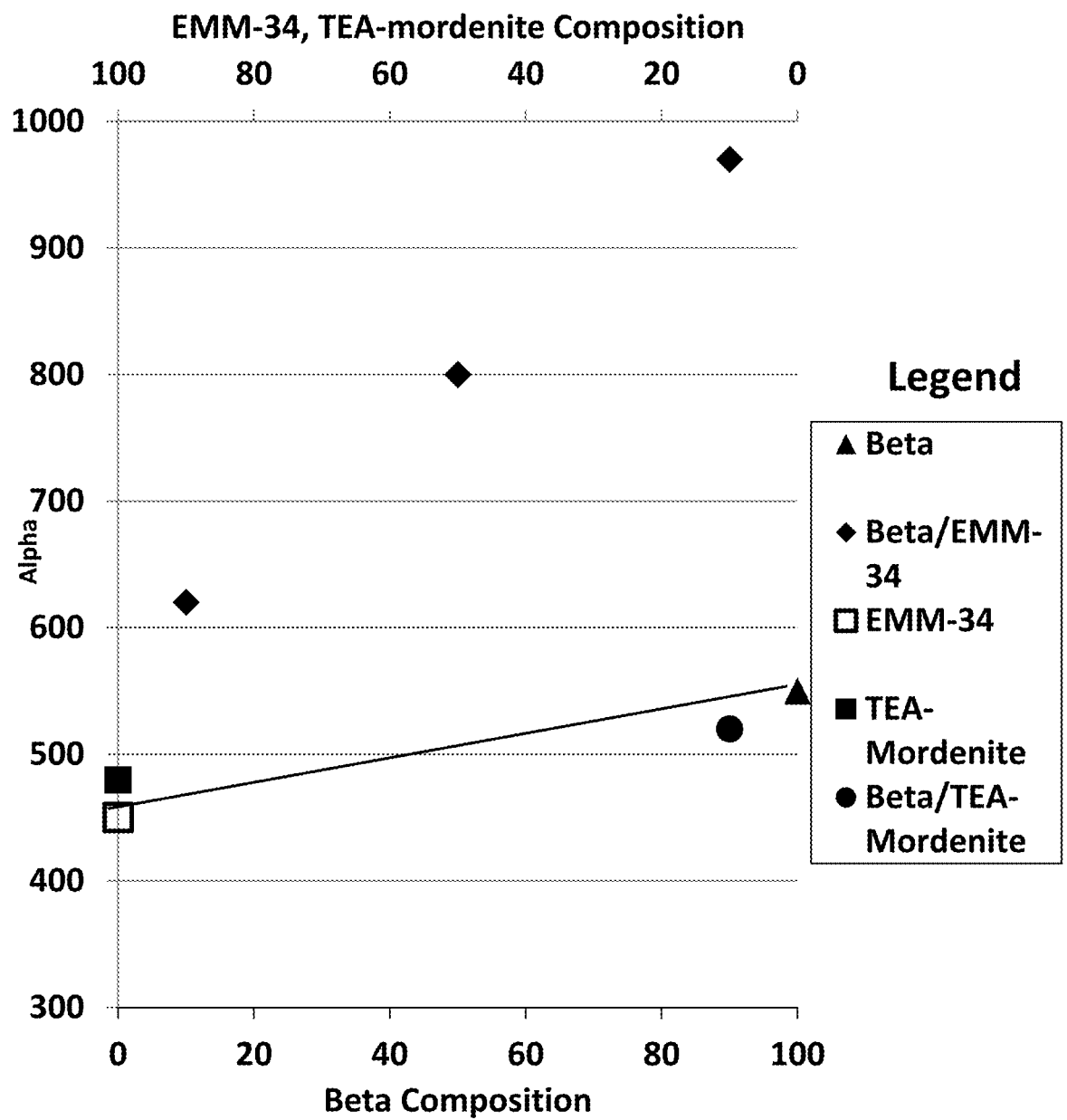
FIG. 1 shows the performance of the catalyst compositions of Example 5 as measured by the Alpha Value plotted as a function of the zeolite beta, EMM-34 or TEA-mordenite content of the catalyst composition.

Increased capacity to adsorb catalyst poisons from hydrocarbons streams is to exhibited by the catalyst composition of this invention, described herein, when used in a process for producing a mono-alkylated aromatic compound, preferably ethylbenzene or cumene, by the alkylation of alkylatable aromatic compound, preferably benzene, with an with an alkylating agent, preferably ethylene or propylene, in the presence of such composition under at least partial liquid phase conditions.

Definitions

The term "catalyst compound" as used herein, includes a material that can act to increase the rate constant in a chemical reaction, as well as a material that can act to adsorb catalyst poisons from a hydrocarbon stream.

The term "alkylatable aromatic compound" as used herein, means an aromatic compound that may receive an alkyl group. One non-limiting example of an alkylatable aromatic compound is benzene.

The term "alkylating agent" as used herein, means a compound which may donate an alkyl group to an alkylatable aromatic compound. Non-limiting examples of an alkylating agent are ethylene, propylene, and butylene. Another non-limiting example is any poly-alkylated aromatic compound that is capable of donating an alkyl group to an alkylatable aromatic compound.

The term "aromatic" as used herein, in reference to the alkylatable aromatic compounds which are useful herein, is to be understood in accordance with its art-recognized scope which includes substituted and unsubstituted mono- and polynuclear compounds. Compounds of an aromatic character which possess a heteroatom (e.g., N or S) are also useful provided they do not act as catalyst poisons, as defined below, under the reaction conditions selected.

The term "at least partial liquid phase" as used herein, means a mixture having at least 1 wt. % liquid phase, optionally at least 5 wt. % liquid phase, at a given temperature, pressure, and composition.

The term "catalyst poisons" as used herein, means one or more impurities, defined herein, which acts to reduce the cycle-length of a molecular sieve or zeolite.

As used herein, the term "constraint index" is defined in U.S. Pat. Nos. 3,972,832 and 4,016,218.

The term "framework type" as used herein has the meaning described in the "Atlas of Zeolite Framework Types," by Ch. Baerlocher, W. M. Meier and D. H. Olson (Elsevier, 5th Ed., 2001). The BEA* framework type includes various forms of zeolite beta. The MOR framework type includes various forms of mordenite such as, for example, TEA-mordenite, EMM-34 and UZM-14.

Zeolite beta is described in U.S. Pat. No. 3,308,069 and U.S. Reissue Pat. No. 28,341. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. EMM-34, also referred to as meso-mordenite, is a zeolite synthesized from structure directing agents TEA (tetraethyl ammonium cation) or MTEA (methyl triethyl ammonium cation) and having a mesopore surface area of greater than 30 m$^2$/g and comprising agglomerates composed of primary crystallites, wherein the primary crystallites have an average primary crystal size as measured by TEM of less than 80 nm and an aspect ratio of less than 2, as disclosed in International Publication WO2016/126431, incorporated by reference where permitted. UZM-14 is described in U.S. Publication 20090325785 A1

The term "MCM-22 family material" (or "MCM-22 family molecular sieve"), as used herein, can include:
  (i) molecular sieves made from a common first degree crystalline building block "unit cell having the MWW framework topology." A unit cell is a spatial arrangement of atoms which is tiled in three-dimensional space to describe the crystal as described in the "Atlas of Zeolite Framework Types," by Ch. Baerlocher, W. M. Meier and D. H. Olson (Elsevier, 5th Ed., 2001);
  (ii) molecular sieves made from a common second degree building block, a 2-dimensional tiling of such MWW framework type unit cells, forming a "monolayer of one unit cell thickness," preferably one c-unit cell thickness;
  (iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof; or
  (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system.

Members of the MCM-22 family include, but are not limited to, MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), MCM-56 (described in U.S. Pat. No. 5,362,697; and an EMM-10 family molecular sieve (described or characterized in U.S. Pat. Nos. 7,959,899 and 8,110,176; and U.S. Patent Application Publication No. 2008/0045768), such as EMM-10, EMM-10-P, EMM-12 and EMM-13. Typically, the molecular sieve of the MCM-22 family is in the hydrogen form and having hydrogen ions, for example, acidic.

Related zeolites to be included in the MCM-22 family are UZM-8 (described in U.S. Pat. No. 6,756,030), UZM-8HS (described in U.S. Pat. No. 7,713,513), UZM-37 (described in U.S. Pat. No. 8,158,105), and MIT-1 is described in Chem. Sci., 2015, 6, 6320-6324, all of which are also suitable for use as the molecular sieve of the MCM-22 family.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n, where n is the number of carbon atom(s) per molecule.

The term "mono-alkylated aromatic compound" means an aromatic compound that has only one alkyl substituent. Non-limiting examples of mono-alkylated aromatic compounds are ethylbenzene, iso-propylbenzene (cumene) and sec-butylbenzene.

The term "poly-alkylated aromatic compound" as used herein, means an aromatic compound that has more than one alkyl substituent. A non-limiting example of a poly-alkylated aromatic compound is poly-ethylbenzene, e.g., di-ethylbenzene, tri-ethylbenzene, and poly-isopropylbenzene, e.g., di-isopropylbenzene, and tri-isopropylbenzene.

The term "impurities" as used herein, includes, but is not limited to, compounds having at least one of the following elements: nitrogen, halogens, oxygen, sulfur, arsenic, selenium, tellurium, phosphorus, and Group 1 through Group 12 metals.

The term "large pore molecular sieve" as used herein, means molecular sieve having a Constraint Index of less than 2.

Suitable large pore molecular sieves include zeolite beta, zeolite Y, Ultrastable Y (USY), Dealuminized Y (Deal Y), Ultrahydrophobic Y (UHP-Y), Rare earth exchanged Y (REY), mordenite, TEA-mordenite, ZSM-2, ZSM-3, ZSM-4, ZSM-14, ZSM-18 and ZSM-20. Zeolite ZSM-2 is described in U.S. Pat. No. 3,411,874. Zeolite ZSM-3 is described in U.S. Pat. No. 3,415,736. ZSM-4 is described in U.S. Pat. No. 4,021,447. ZSM-14 is described in U.S. Pat. No. 3,923,636. ZSM-18 is described in U.S. Pat. No. 3,950,496. Zeolite ZSM-20 is described in U.S. Pat. No. 3,972,983. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Ultrahydrophobic Y (UHP-Y) is described in U.S. Pat. No. 4,401,556. Rare earth exchanged Y (REY) is described in U.S. Pat. No. 3,524,820. ECR-4 is described in U.S. Pat. No. 4,965,059. ECR-17 is described in EP Publication EP0259526. ECR-32 is described in U.S. Pat. No. 4,931,267. ECR-35 is described in U.S. Pat. No. 5,116,590.

The term "comprising" (and its grammatical variations) as used herein, is used in the inclusive sense of "having" or "including" and not in the exclusive sense of "consisting only of." The terms "a" and "the" as used herein are understood to encompass the plural as well as the singular.

The entire contents of each and every aforementioned patents and publications are incorporated herein by reference in their entireties.

Catalyst Composition

The first aspect of this invention is a catalyst composition which comprises a first zeolite having a BEA* framework type and a second zeolite having a MOR framework type. The first zeolite can be zeolite beta. The second zeolite can be any one of TEA-mordenite, EMM-34, UZM-14 or combinations of two or more thereof. TEA-mordenite, EMM-34 and UZM-14 are described in the publications, referenced above.

In one or more embodiments, EMM-34 has a mesopore surface area of greater than 30 $m^2/g$ (as measured by BET) and comprising agglomerates composed of primary crystallites, wherein the primary crystallites have an average primary crystal size as measured by TEM of less than 80 nm, an aspect ratio of less than 2 and a total surface area of greater than 500 $m^2/g$ (as measured by BET)

In some embodiments, EMM-34 has a ratio of the mesopore surface area to the total surface area of greater than 0.05, and is synthesized from TEA or MTEA.

The EMM-34 has a mesopore surface area as measured by BET of greater than 30 $m^2/g$, preferably greater than 40 $m^2/g$, and in some cases greater than 45 $m^2/g$.

EMM-34 comprises agglomerates, typically irregular agglomerates, which are composed of primary crystallites which have an average primary crystal size as measured by TEM of less than 80 nm, preferably less than 70 nm and more preferably less than 60 nm, for example, less than 50 nm. The primary crystallites may have an average primary crystal size in the range of greater than 20 nm, optionally greater than 30 nm to less than 80 nm as measured by TEM.

Optionally, the primary crystals of EMM-34 have an average primary crystal size of less than 80 nm, preferably less than 70 nm, and in some cases less than 60 nm, in each of the a, b and c crystal vectors as measured by X-ray diffraction. The primary crystallites may optionally have an average primary crystal size in the range of greater than 20 nm, optionally greater than 30 nm to less than 80 nm, in each of the a, b and c crystal vectors, as measured by X-ray diffraction.

EMM-34 will generally comprise a mixture of agglomerates of the primary crystals together with some unagglomerated primary crystals. The majority of EMM-34, for example, greater than 80 weight % or greater than 90 weight %, will be present as agglomerates of primary crystals. The agglomerates are typically of irregular form. For more information on agglomerates please see Walter, D. (2013) Primary Particles—Agglomerates—Aggregates, in Nanomaterials (ed Deutsche Forschungsgemeinschaft (DFG)), Wiley-VCH Verlag GmbH & Co. KGaA, Weinheim, Germany. doi: 10.1002/9783527673919, pages 1-24. Usefully, EMM-34 is not an aggregate.

Optionally, EMM-34 comprises at least 50% by weight, preferably at least 70% by weight, advantageously at least 80% by weight, more preferably at least 90% by weight and optionally substantially consists of the irregular agglomerates composed of primary crystallites having a primary crystal size of less than 80 nm, preferably less than 70 nm, and more preferably less than 60 nm, for example, less than 50 nm. Preferably, EMM-34 comprises less than 10% by weight of primary crystallites having a size of more than 80 nm as assessed by TEM. Preferably, EMM-34 is composed of the irregular agglomerates composed of crystallites having a crystal size as measured by TEM of less than 80 nm. Preferably, EMM-34 of the invention is substantially free, for example, contains less than 10% by number as assessed by TEM, of needle or platelet crystals.

Preferably, the primary crystallites of EMM-34 have an aspect ratio of less than 3.0, more preferably less than 2.0, wherein the aspect ratio is defined as the longest dimension of the crystallite divided by the width of the crystallite, where the width of the crystallite is defined as the dimension of the crystallite in the middle of that longest dimension in a direction orthogonal to that longest dimension, as measured by TEM.

The agglomerates of the primary crystallites are typically of irregular form and may be referred to as being "secondary" particles because they are formed of agglomerates of the crystallites, which are the "primary" particles.

The primary crystallites may have a narrow particle size distribution such that at least 90% of the primary crystallites by number have an average primary crystal size in the range of from 20 to 80 nm, preferably in the range of from 20 to 60 nm, as measured by TEM.

EMM-34 has a total surface area of greater than 500 $m^2/g$, more preferably greater than 550 $m^2/g$, and in some cases greater than 600 $m^2/g$. The total surface area includes the surface area of the internal pores (zeolite surface area) and also the surface area on the outside of the crystals (the external surface area). The total surface area is measured by BET.

Preferably, the ratio of mesopore surface area to the total surface area for EMM-34 is greater than 0.05.

EMM-34 has a mesopore volume of greater than 0.1 mL/g, more preferably greater than 0.12 mL/g, and in some cases greater than 0.15 mL/g.

The silica-alumina molar ratio (Si:$Al_2$ molar ratio) of the second zeolite, such as EMM-34, is preferably greater than 10 and may be in the range of, for example, from 10 to 60, preferably from 15 to 40.

The silica-alumina molar ratio (Si:$Al_2$ molar ratio) of the first zeolite, such as zeolite beta, is preferably lower than 50 and may be in the range of, for example, from 15 to 50, preferably from 15 to 25.

For the catalyst compositions of this invention, the ratio of the first zeolite to the second zeolite is in the range of 90:10 to 50:50, or 80:20 to 50:50, or 70:30 to 50:50, or 60:40 to 50:50 by weight of the catalyst composition.

The Si/$Al_2$ molar ratio (silica-alumina molar ratio) of the second zeolite of the catalyst composition, EMM-34 in some embodiments, is in the range of 10 to 60 or 20 to 60 or 30 to 60.

The collidine uptake of the catalyst composition can greater than 500 μmoles/g or in the range of 550 μmoles/g to 1500 μmoles/g, or in the range of 550 μmoles/g to 700 μmoles/g.

In one or more embodiments, the catalyst composition of this invention can be made by a method such the first zeolite and the second zeolite are co-crystallized in the same synthesis mixture.

In one or more embodiments, the catalyst composition can be made by a method such that the first zeolite is co-extruded with the second zeolite. In this method, the first zeolite, such as zeolite beta, is combined with the second zeolite, such as EMM-34, in a muller or a mixer and mixed for a period of time, such as 10 to 30 minutes. Sufficient water is added to produce an extrudable paste which is then extruded into a shaped extrudate, such as in the shape of a cylinder or quadrulobe. The extrudate may then be dried at an elevated temperature, such as, for example, from 121° C. to 163° C. The dried extrudate may then be calcined at high temperature, such as, for example, at 538° C., under flowing air, nitrogen, a nitrogen/air mixture, or other gas. The dried extrudate may then be cooled to ambient temperature, and may be humidified with saturated air or steam. After the humidification, the extrudate is typically ion exchanged with 0.5 to 1 N ammonium nitrate solution, for example, and then washed with deionized water, for example, to remove residual ions, such as nitrate, for example, and then dried. The dried, exchanged extrudate is then calcined in air, nitrogen, a nitrogen/air mixture or other gas, at a temperature, for example, between 850° F. (454° C.) and 1100° F. (593° C.).

Method for Removing Impurities from Hydrocarbon Streams

The second aspect of this invention is a method for removing impurities from a hydrocarbon stream. The method comprises step (a) of providing a guard bed catalyst, preferably in a guard bed and having the guard bed catalyst disposed therein. The guard bed catalyst comprises any one of the catalyst composition of this invention, described herein. In step (b) of the method, at least a portion of a feed stream is supplied to the guard bed. The feed stream comprises one or more hydrocarbons and undesirable impurities. The impurities comprise at least one compound having at least one of the following elements: nitrogen, halogens, oxygen, sulfur, arsenic, selenium, tellurium, phosphorus, and Group 1 through Group 12 metals. In step (c) of the method, the portion of the feed stream is contacted with the guard bed catalyst to remove at least a portion of the impurities and produce a treated feed stream having a reduced amount of impurities.

Process for Producing Mono-Alkylated Aromatic Compounds

The third aspect of this invention is a process for producing a mono-alkylated aromatic compound. The process comprises step (a) of providing a guard bed catalyst, preferably, in a guard bed wherein the guard bed catalyst is disposed therein. The guard bed catalyst comprises any one of the catalyst compositions of this invention. In step (b) of the process, at least a portion of an untreated feed stream is supplied to the guard bed. In this step, the guard bed is a non-reactive guard bed because no alkylating agent is present. The untreated feed stream comprises an alkylatable aromatic compound and undesirable impurities, as defined herein. Such impurities act as catalyst poisons to the downstream alkylation catalyst and/or transalkylation catalyst, and thereby reduce the service life (e.g., cycle length) of these catalysts. In step (c) of the process, the portion of the untreated feed stream of step (b) is contacted with the guard bed catalyst to remove at least a portion of the impurities and produce a treated feed stream having a reduced amount of impurities. In step (d) of the process, at least a portion of the treated feed stream having a reduced amount of impurities and an alkylating agent stream are contacted in the presence or with an alkylation catalyst which is the same or different from the guard bed catalyst. The contacting is under suitable at least partially liquid phase reaction conditions to alkylate at least a portion of the alkylatable aromatic compound with the alkylating agent stream to produce an effluent stream. Such effluent stream comprises the mono-alkylated aromatic compound and poly-alkylated aromatic compounds. The reduced amount of impurities in the treated feed stream subjects the downstream alkylation and transalkylation catalysts to fewer catalyst poisons and enables longer service life for these downstream catalysts.

The step (b) can further include supplying an alkylating agent stream to the guard bed. The alkylating agent stream is contacted with the alkylatable aromatic compound in the presence of the guard bed catalyst to produce additional the mono-alkylated aromatic compound. In this embodiment, the guard bed is a reactive guard bed in which an alkylating agent stream is present. This results in an alkylated aromatic compound being produced via an alkylation reaction between the alkylatable aromatic compound and alkylating agent and at the same time at least a portion of the impurities are removed from the feed stream via adsorption by the guard bed catalyst.

The effluent stream of step (d) can be separated to recover a mono-alkylated aromatic compound stream and a poly-alkylated aromatic compounds stream in a step (e). The poly-alkylated aromatic compound stream can be transalkylated with an alkylatable aromatic compound to produce additional mono-alkylated aromatic compound in a step (f). This is done by contacting the poly-alkylated aromatic compound and another portion of the feed stream, such as the untreated feed stream of step (b), in the presence or with a transalkylation catalyst under suitable at least partially liquid phase transalkylation conditions to transalkylate the poly-alkylated aromatic compound stream with the alkylatable aromatic compound and produce additional the mono-alkylated aromatic compound.

Alternatively, prior to step (f), the portion of the untreated feed stream is first contacted with a guard bed catalyst to remove at least a portion of the impurities to form a treated feed stream. The guard bed catalyst comprises any one of the catalyst compositions of this invention.

In the embodiments of the invention, when the alkylatable aromatic compound is benzene and the alkylating agent is propylene, the mono-alkylated aromatic compound is ethylbenzene and the poly-alkylated aromatic compound is poly-ethylbenzene.

In the embodiments of the invention, when the alkylatable aromatic compound is benzene and the alkylating agent is ethylene, the mono-alkylated aromatic compound is cumene and the poly-alkylated aromatic compound is poly-isopropylbenzene.

Alkylation Catalyst and Transalkylation Catalyst

In one or more embodiments, the alkylation catalyst comprises an aluminosilicate. The aluminosilicate is any one of a MCM-22 family molecular sieve, faujasite, mordenite, zeolite beta, or combinations of two or more thereof, which has been found to be useful in processes for production of mono-alkylated aromatic compounds.

In one or more embodiments, the MCM-22 family molecular sieve is selected from the group consisting of MCM-22, MCM-36, MCM-49, MCM-56, ERB-1, EMM-10, EMM-10-P, EMM-12, EMM-13, UZM-8, UZM-8HS, UZM-37, ITQ-1, ITQ-2, ITQ-30, MIT-1, or combinations of two or more thereof.

In other embodiments, the transalkylation catalyst is a large pore molecular sieve having a constraint index of less than 2. The large pore molecular sieve is selected from the group of consisting of zeolite beta, faujasite, mordenite, TEA-mordenite, EMM-34, ZSM-2, ZSM-3, ZSM-4, ZSM-14, ZSM-18, ZSM-20, ECR-4, ECR-17, ECR-32, ECR-35 and combinations thereof. The faujasite large pore molecular sieve is selected from the group consisting of 13X, low sodium ultrastable Y (USY), dealuminized Y (Deal Y), ultrahydrophobic Y (UHP-Y), rare earth exchanged Y (REY), rare earth exchanged USY (RE-USY), and mixtures thereof.

The molecular sieve of the alkylation catalyst and/or the transalkylation catalyst can be combined in conventional manner with an oxide binder, such as alumina or silica, such that the final alkylation catalyst and/or transalkylation contains between 1 and 100 wt. % of the molecular sieve.

Alkylatable Aromatic Compounds

Substituted alkylatable aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable alkylatable aromatic hydrocarbons for any one of the embodiments of this invention include benzene, naphthalene, anthracene, naphthacene, perylene, coronene, and phenanthrene, with benzene being preferred.

Generally the alkyl groups, which can be present as substituents on the aromatic compound, contain from 1 to about 22 carbon atoms and usually from about 1 to 8 carbon atoms, and most usually from about 1 to 4 carbon atoms.

Suitable alkyl substituted aromatic compounds for any one of the embodiments of this invention include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetraethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalene; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing substantial quantities of benzene, toluene and/or xylene constitutes a useful feed for the process of this invention.

Alkylating Agents

The alkylating agents, which are useful in one or more embodiments of this invention, generally include any aliphatic or aromatic organic compound having one or more available alkylating olefinic groups capable of reaction with the alkylatable aromatic compound, preferably with the alkylating group possessing from 1 to 5 carbon atoms, or poly-alkylated aromatics compound(s). Examples of suitable alkylating agents for any one of the embodiments of this invention are olefins such as ethylene, propylene, the butenes, and the pentenes; alcohols (inclusive of monoalcohols, dialcohols, trialcohols, etc.), such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein.

Poly-alkylated aromatic compounds suitable for one or more embodiments of this invention include, but are not limited to, polyethylbenzene(s), polyisporpoylebenzene(s) or mixtures thereof.

For example, a typical FCC light olefin stream possesses the following composition as shown in Table I:

TABLE I

| | Wt. % | Mol. % |
|---|---|---|
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-butane | 3.3 | 2.6 |
| Butenes | 22.1 | 18.32 |
| Pentanes | 0.7 | 0.4 |

Alkylation and/or Transalkylation Conditions

In one or more embodiments, the alkylation and/or transalkylation processes of this invention is conducted such that the organic reactants, i.e., the alkylatable aromatic compound and the alkylating agent, are brought into contact with an alkylation or transalkylation catalyst in a suitable alkylation or transalkylation reaction zone such as, for example, in a flow reactor containing a fixed bed of the catalyst composition, under effective and suitable alkylation and/or transalkylation conditions.

Such alkylation conditions can include at least one of the following: a temperature of from about 10° C. and about 400° C., or from about 10° C. to about 200° C., or from about 150° C. to about 300° C., a pressure up to about 25000 kPa, or up to about 20000 kPa, or from about 100 kPa to about 7000 kPa, or from about 689 kPa to about 4601 kPa, a molar ratio of alkylatable aromatic compound to alkylating agent of from about 0.1:1 to about 50:1, preferably from about 0.5:1 to 10:1, and a feed weight hourly space velocity (WHSV) of between about 0.1 and about 100 $hr^{-1}$, or from about 0.5 to 50 $hr^{-1}$, or from about 10 $hr^{-1}$ to about 100 $hr^{-1}$.

The reactants can be in either the vapor phase or in the liquid phase, or in the at least partially liquid phase. In one or more embodiments, the reactants can be neat, i.e., free from intentional admixture or dilution with other material, or they can include carrier gases or diluents such as, for example, hydrogen or nitrogen.

When benzene is alkylated with ethylene to produce ethylbenzene, the alkylation reaction may be carried out under at least partially liquid phase conditions including a temperature between about 150° C. and 300° C., or between about 200° C. and 260° C., a pressure up to about 20000 kPa, preferably from about 200 kPa to about 5600 kPa, a WHSV of from about 0.1 $hr^{-1}$ to about 50 $hr^{-1}$, or from about 1 $hr^{-1}$ and about 10 $hr^{-1}$ based on the ethylene feed, and a ratio of the benzene to the ethylene in the alkylation reactor from 1:1 to 30:1 molar, preferably from about 1:1 to 10:1 molar.

When benzene is alkylated with propylene to produce cumene, the reaction may be carried out under at least partially liquid phase conditions including a temperature of up to about 250° C., preferably from about 10° C. to about 200° C.; a pressure up to about 25000 kPa, preferably from about 100 kPa to about 3000 kPa; and a WHSV of from about 1 hr$^{-1}$ to about 250 hr$^{-1}$, preferably from 5 hr$^{-1}$ to 50 hr$^{-1}$, preferably from about 5 hr$^{-1}$ to about 10 hr$^{-1}$ based on the ethylene feed.

Such transalkylation conditions can include at least one of the following: a temperature of about 100° C. to about 300° C., or from about 100° C. to about 275° C., a pressure of about 200 kPa to about 600 kPa, or about 200 kPa to about 500 kPa, a weight hourly space velocity (WHSV) based on the total feed of about 0.5 hr$^{-1}$ to about 100 hr$^{-1}$ on total feed, and aromatic/poly-alkylated aromatic compound weight ratio 1:1 to 6:1.

When the poly-alkylated aromatic compounds are polyethylbenzenes and are reacted with benzene to produce ethylbenzene, the transalkylation conditions include a temperature of from about 220° C. to about 260° C., a pressure of from about 300 kPa to about 400 kPa, weight hourly space velocity of 2 to 6 on total feed and benzene/PEB weight ratio 2:1 to 6:1.

When the poly-alkylated aromatic compounds are polyisopropylbenzenes (PIPBs) and are reacted with benzene to produce cumene, the transalkylation conditions include a temperature of from about 100° C. to about 200° C., a pressure of from about 300 kPa to about 400 kPa, a weight hourly space velocity of 1 to 10 on total feed and benzene/PIPB weight ratio 1:1 to 6:1.

EXAMPLES

The invention will now be more particularly described with reference to the following Examples. Numerous modifications and variations are possible and it is to be understood that within the scope of the appended claims, the invention may be practiced otherwise than as specifically described herein.

EXPERIMENTAL

Alpha Value

The alpha value is a measure of the cracking activity of a catalyst composition and is described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test used herein included a constant temperature of 538° C. and a variable flow rate as described in detail in the Journal of Catalysis, Vol. 61, p. 395 (1980).

Collidine Uptake

Collidine uptake is a measure of the acidity of a zeolite or catalyst composition. The collidine uptake of the zeolites and catalyst compositions was determined as the millimoles of collidine (a type of catalyst poison) absorbed per gram of a zeolite or catalyst composition sample that is dried under nitrogen flow at 200° C. for 60 minutes on a Thermogravametric Analyzer (Model Q5000, manufactured by TA Instruments, New Castle, Del.). After drying the catalyst sample, the collidine (as a catalyst poison) was sparged over the catalyst sample for 60 minutes at a collidine partial pressure of 3 torr. The collidine uptake was calculated from the following formula: (catalyst sample weight after sparging with collidine–dried catalyst sample weight)×106÷(molecular weight of collidine×dried catalyst sample weight). When the catalyst sample weight and the dried catalyst sample weight is measured in grams, the molecular weight of collidine is 121.2 grams per millimole.

Temperature Programmed Ammonia Desorption

Temperature programmed ammonia desorption (TPAD) is also a measure of the acidity of a zeolite or catalyst composition. TPAD techniques are well known in the art. For the TPAD analysis, a catalyst sample (0.2 g) was first dried at 500° C. for 3 hours under a helium (He) flow rate of 10 cc/min. The temperature was then reduced to 100° C. whereupon the catalyst sample was saturated with ammonia gas. After saturation with ammonia gas, the catalyst sample was desorbed at 100° C. with helium flow to desorb physisorbed ammonia from the catalyst sample. TPAD was performed at a desorption temperature ramp of 18.4° C./min under helium flow rate of 16 cc/min. The desorbed ammonia and water (if any) were monitored during the TPAD as meq/g.

Example 1: Synthesis of Zeolite Beta

Eighty (80) parts zeolite beta crystals are combined with 20 parts pseudoboehmite alumina, on a calcined dry weight basis. The zeolite beta and pseudoboehmite alumina dry powder are placed in a muller or a mixer and mixed for about 10 to 30 minutes. Sufficient water is added to the zeolite beta and alumina during the mixing process to produce an extrudable paste. The extrudable paste is formed into a ¹⁄₂₀ inch quadrulobe extrudate using an extruder. After extrusion, the ¹⁄₂₀th inch quadrulobe extrudate is dried at a temperature ranging from 250° F. (121° C.) to 325° F. (168° C.). The dried extrudate is then calcined in a nitrogen/air mixture to a temperature between 850° F. (454° C.) and 1100° F. (593° C.).

Example 2: Synthesis of EMM-34 Zeolite

Eighty (80) parts EMM-34 zeolite crystals were combined with 20 parts pseudoboehmite alumina, on a calcined dry weight basis. The EMM-34 and pseudoboehmite alumina dry powder were placed in a muller or a mixer and mixed for about 10 to 30 minutes. Sufficient water was added to the EMM-34 and alumina during the mixing process to produce an extrudable paste. The extrudable paste was formed into a ¹⁄₂₀ inch quadrulobe extrudate using an extruder. After extrusion, the ¹⁄₂₀th inch quadrulobe extrudate was dried at a temperature ranging from 250° F. (121° C.) to 325° F. (168° C.). After drying, the dried extrudate was heated to 1000° F. (538° C.) under flowing nitrogen. The extrudate was then cooled to ambient temperature and humidified with saturated air or steam. After the humidification, the extrudate was ion exchanged with 0.5 to 1 N ammonium nitrate solution. The ammonium nitrate solution ion exchange was repeated. The ammonium nitrate exchanged extrudate was then washed with deionized water to remove residual nitrate prior to calcination in air. After washing the wet extrudate, it was dried. The exchanged and dried extrudate was then calcined in a nitrogen/air mixture to a temperature between 850° F. (454° C.) and 1100° F. (593° C.).

Example 3: Synthesis of TEA-Mordenite Zeolite

Eighty (80) parts TEA-mordenite zeolite crystals were combined with 20 parts pseudoboehmite alumina, on a calcined dry weight basis. The mordenite and pseudoboehmite alumina dry powder was placed in a muller or a mixer and mixed for about 10 to 30 minutes. Sufficient water was added to the mordenite and alumina during the mixing process to produce an extrudable paste. The extrudable paste was formed into a ¹⁄₂₀ inch quadrulobe extrudate using an extruder. After extrusion, the ¹⁄₂₀th inch quadrulobe extrudate was dried at a temperature ranging from 250° F. (121° C.) to 325° F. (168° C.). After drying, the dried extrudate is heated to 1000° F. (538° C.) under flowing nitrogen. The extrudate was then cooled to ambient temperature and humidified with saturated air or steam. After the humidification, the extrudate was ion exchanged with 0.5 to 1 N ammonium nitrate solution. The ammonium nitrate solution ion exchange was repeated. The ammonium nitrate exchanged extrudate was then washed with deionized water to remove residual nitrate prior to calcination in air. After washing the wet extrudate, it was dried. The exchanged and dried extrudate was then calcined in a nitrogen/air mixture to a temperature between 850° F. (454° C.) and 1100° F. (593° C.).

Example 4: Synthesis of Mixed Zeolite Catalyst Composition

EMM-34 and zeolite beta crystals were combined in a number of various ratios with 20 parts pseudoboehmite alumina, on a calcined dry weight basis. The EMM-34, zeolite beta, and pseudoboehmite alumina dry powder were placed in a muller or a mixer and mixed for about 10 to 30 minutes. Sufficient water was added during the mixing process to produce an extrudable paste. The extrudable paste was formed into a 1/20 inch quadrulobe extrudate using an extruder. After extrusion, the 1/20th inch quadrulobe extrudate was dried at a temperature ranging from 250° F. (121° C.) to 325° F. (168° C.). After drying, the dried extrudate was heated to 1000° F. (538° C.) under flowing nitrogen. The extrudate was then cooled to ambient temperature and humidified with saturated air or steam. After the humidification, the extrudate was ion exchanged with 0.5 to 1 N ammonium nitrate solution. The ammonium nitrate solution ion exchange was repeated. The ammonium nitrate exchanged extrudate was then washed with deionized water to remove residual nitrate prior to calcination in air. After washing the wet extrudate, it was dried. The exchanged and dried extrudate was then calcined in a nitrogen/air mixture to a temperature between 850° F. (454° C.) and 1100° F. (593° C.).

The zeolites and catalyst compositions materials described above were characterized for poison capacity when deployed in a guard bed (GB), such as a reactive guard bed (RGB) or a non-reactive guard bed, during alkylation service by testing them for their acidity or amount of acid sites. These acid sites are known in the art for providing the poison capacity in GB service. One way to measure catalyst acidity is by its Alpha Value or a standard hexane cracking test. A second way to measure acidity of a material is to determine the total uptake of collidine on a mass basis. A third way to measure acidity of a material is to adsorb ammonia on the material at a particular temperature, and then determine the amount of ammonia desorbed from that material as the temperature is increased.

For the Figures used herein, the composition numbers on the x-axis are the percentage of a particular zeolite in the formed extrudate. The "linear trend" line is what would be expected if the addition of EMM-34 and zeolite beta to the formed extrudate was purely an additive effect. Any deviation from the "linear trend" would be an unexpected result.

Example 5: Performance Testing—Alpha Value

The results of the alpha test in FIG. 1 below show a linear trend line drawn between a 100 wt. % EMM-34 and 100 wt. % zeolite beta. While the 100 wt. % TEA-mordenite and the mixed zeolite 10 wt. % TEA-mordenite/90 wt. % zeolite beta essentially fall on the linear trend line, the mixed zeolite combinations of EMM-34 and zeolite beta deviate significantly from the trend line and have higher acidity (and higher hexane cracking activity). This unexpected result shows a significant advantage for the 10 wt. % EMM-34/90 wt. % zeolite beta catalyst composition of mixed zeolite formulation for GB service.

Example 6: Performance Testing—Collidine Uptake

Figure 2:
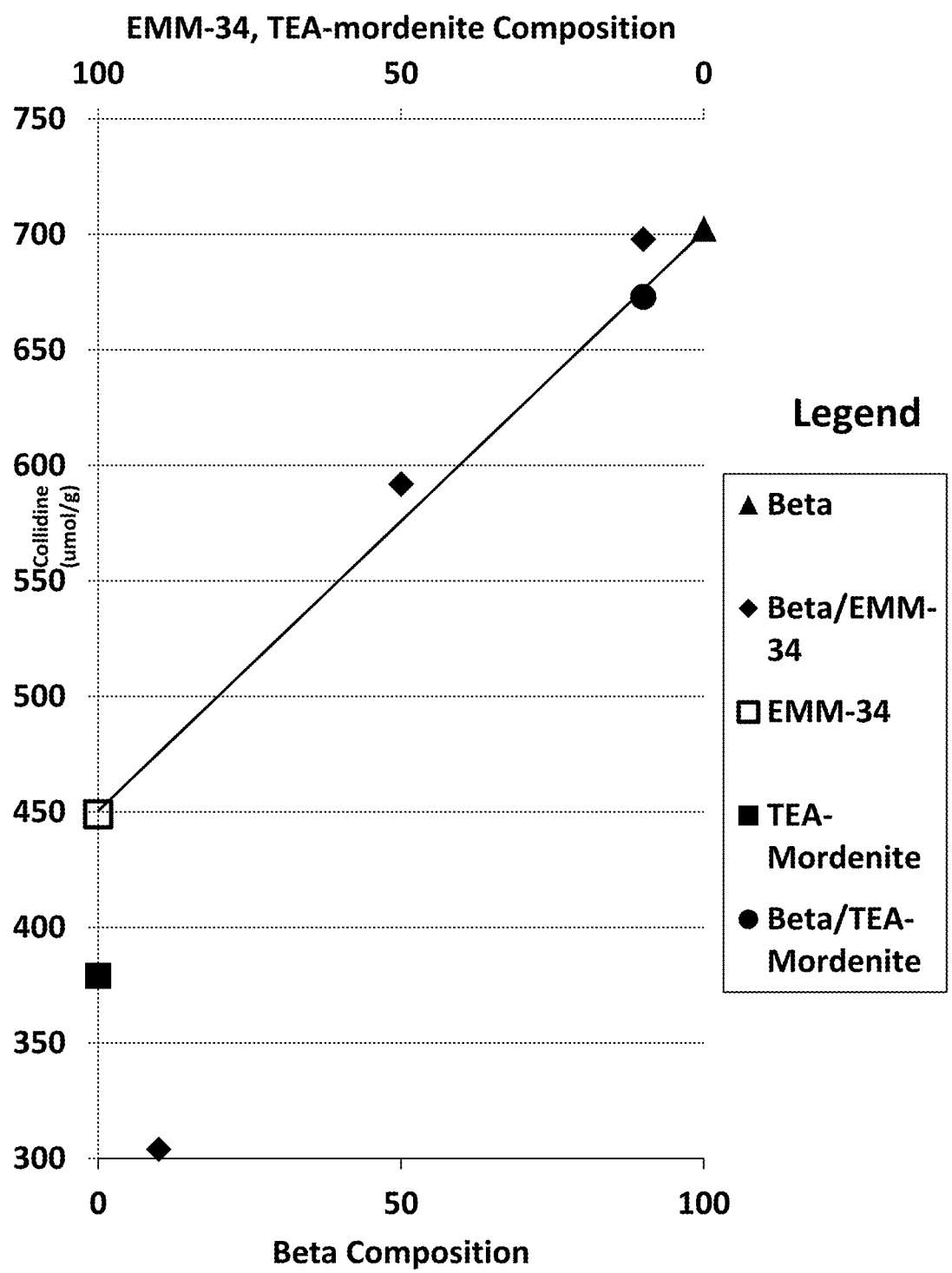
FIG. 2 shows the performance of the catalyst compositions of Example 6 as measured by collidine uptake plotted as a function of the zeolite beta, EMM-34 or TEA-mordenite content of the catalyst composition.

The results of the collidine uptake test in FIG. 2 show a linear trend line drawn between a 100 wt. % EMM-34 and a 100 wt. % zeolite beta. While the 100 wt. % TEA-mordenite and the mixed zeolite 10 wt. % TEA-mordenite/90 wt. % zeolite beta essentially fall on the linear trend line, the mixed zeolite combinations of EMM-34 and zeolite beta deviate significantly from the trend line. The unexpected results show that the 90 wt. % EMM-34/10 wt. % zeolite beta has a lower collidine uptake, while the 50 wt. % EMM-34/50% zeolite beta and the 10 wt. % EMM-34 and 90 wt. % zeolite beta have a higher collidine uptake. This unexpected result shows an advantage for the combinations of EMM-34 and zeolite beta of 50 wt. %/50 wt. % and higher amounts of zeolite beta.

Example 7: Performance Testing—Temperature Programmed Ammonia Desorption

Figure 3:
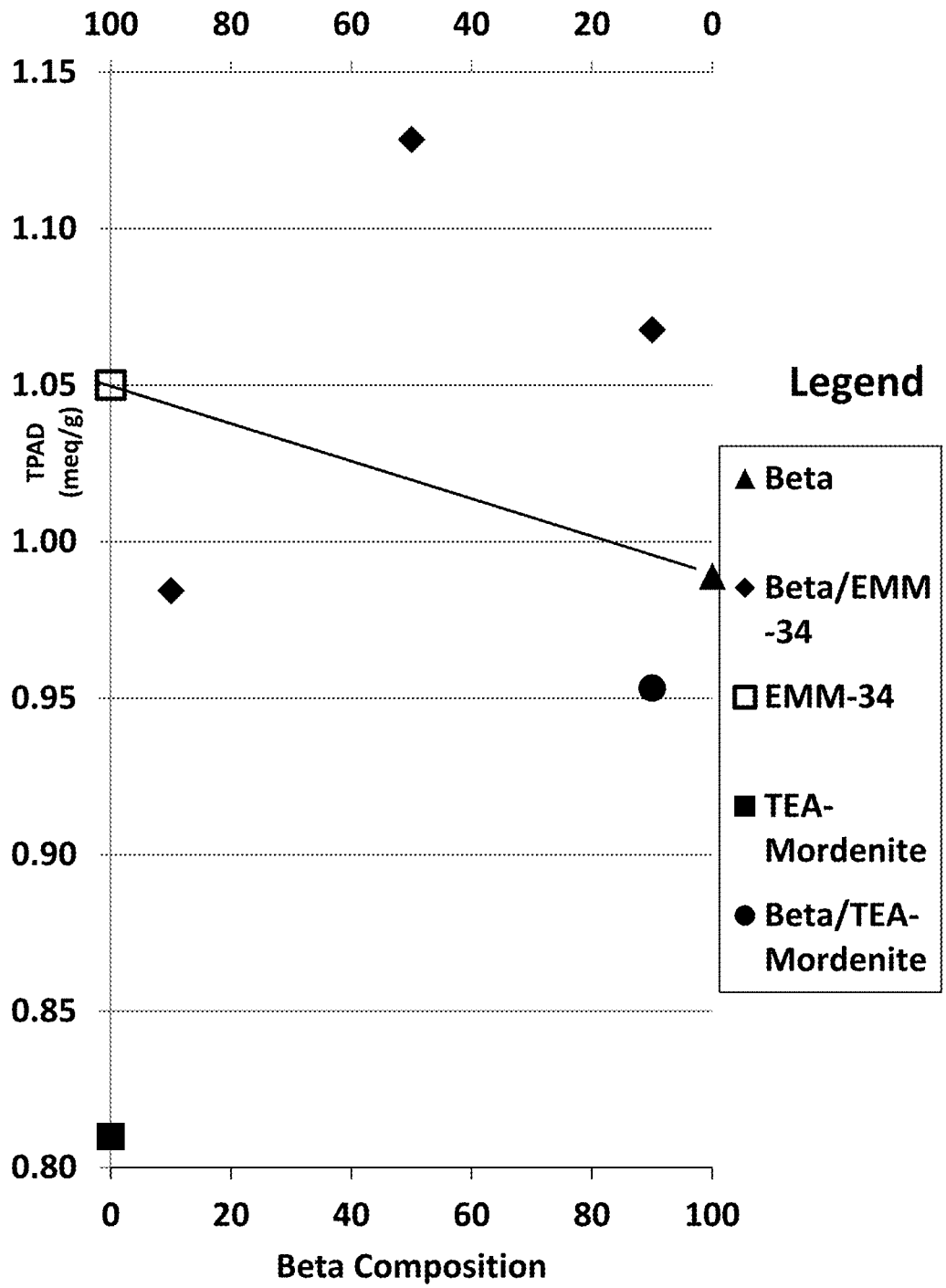
FIG. 3 shows the performance of the catalyst compositions of Example 7 as measured by Temperature Programmed Ammonia Desorption as a function of the zeolite beta, EMM-34 or TEA-mordenite content of the catalyst composition.

The results of the temperature programmed ammonia desorption (TPAD) test in FIG. 3 show a linear trend line drawn between a 100% EMM-34 and 100% zeolite beta. The EMM-34 has a higher TPAD than does the zeolite beta material and thus the linear trend line has a negative slope. In this case, the TEA-mordenite has an inherently lower TPAD and thus a second "Mordenite Linear Trend" has been drawn between 100% TEA-mordenite and 100% zeolite beta materials that have a positive slope. The mixed zeolite 10% TEA-mordenite/90% zeolite beta material has a TPAD value that sits close to the "Mordenite Linear Trend" line. The unexpected results show that the 90% EMM-34/10% zeolite beta material has a lower TPAD, while the 50% EMM-34/50% zeolite beta and the 10% EMM-34 and 90% zeolite beta materials have a higher TPAD. This unexpected result shows an advantage for the combinations of EMM-34 and zeolite beta of 50/50 and higher amounts of zeolite beta.

Example 8: Amorphous Silica as Silica Source and TEA-OH as SDA 626.2 g of water was weighed out. 74.5 g of 50 wt. % NaOH and 10.1 g 35 wt. % TEA-OH (SDA) was added to the water to form a solution. The solution was stirred until the solution was clear. 83.1 g of 27% $Al_2(SO_4)_3$ was added slowly to the solution. 1.4 g of NaCl was dissolved in 20 g of water. 7.2 g of zeolite beta seeds were added to the solution. The solution was mixed for 5-10 minutes. 186.5 g of amorphous silica (Hi-Sil 233™, obtainable from PPG) was added slowly to the solution to form a slurry. 322.6 g of 50 wt. % TEA-Br and the NaCl solution was added to the slurry to form a gel. The gel was thoroughly mixed prior to charging to a stirred autoclave, and stirred at 250 rpm at 140° C. for 120 hours. The nominal gel molar composition parameters were as follows:

$SiO_2/Al_2O_3$=41.38

Na (Alkali)/$SiO_2$=0.34

SDA/$SiO_2$=0.29

OH—/SiO$_2$=0.35

H$_2$O/SiO$_2$=18.84

Figure 4:
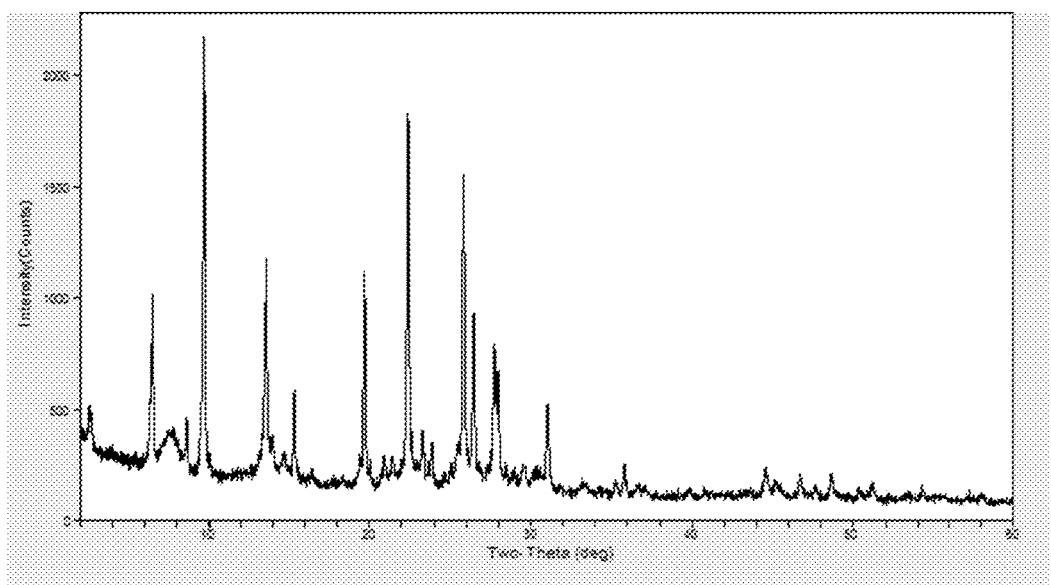
FIG. 4 is the X-ray diffraction pattern for Example 8.

The X-ray diffraction (XRD) pattern, as shown in FIG. 4, indicates that the product that was isolated from the autoclave was a mixture of zeolite beta and mordenite where the amount of zeolite beta in the product was approximately 6%. After pre-calcination, ammonium ion exchange, and calcination at 550° C. the collidine uptake was 367 μmoles/g.

Example 9: Precipitated Silica as Silica Source, TEA-BR as SDA, TEA/Na=0.899

74.6 g of 50 wt. % NaOH was diluted in 641.5 g of water. The solution was stirred until it was clear. 84.2 g of 27% Al$_2$(SO$_4$)$_3$ solution was slowly added to the hydroxide solution. 7.3 g of zeolite beta seeds was added to the solution, and mixed for 5-10 minutes. 175.9 g of a precipitated silica (Ultrasil PM modified silica, obtainable from Evonik) was slowly added to the solution to form a slurry. 352.8 g of 50 wt. % TEA-Br was added to the slurry to form a gel. The gel was thoroughly mixed prior to charging to a stirred autoclave, and stirred at 250 rpm at 140° C. for 120 hours. The nominal gel molar composition parameters were as follows:

SiO$_2$/Al$_2$O$_3$=40.7

Na (alkali)/SiO$_2$=0.343

SDA/SiO$_2$=0.305

TEA/Na=0.899

OH$^-$/SiO$_2$=0.343

H$_2$O/SiO$_2$=18.95

Figure 5:
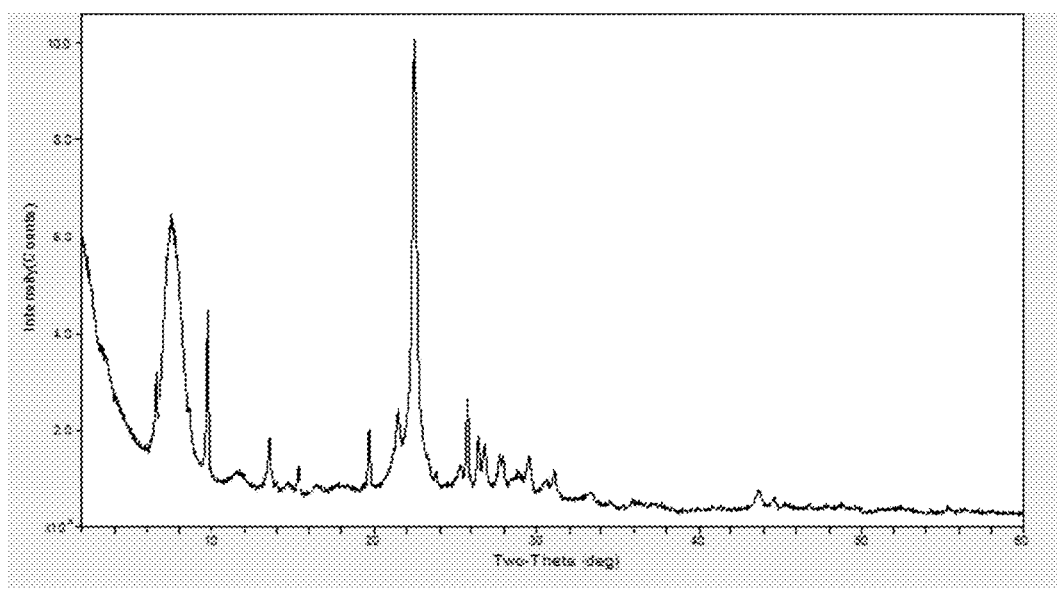
FIG. 5 is the X-ray diffraction pattern for Example 9.

The XRD pattern, as shown in FIG. 5, indicates that the product that was isolated from the autoclave was a mixture of zeolite beta and mordenite where the amount of zeolite beta in the product was approximately 60%.

Example 10: Precipitated Silica as Silica Source, TEA-BR as SDA, TEA/Na=1.11

74.1 g of 50 wt. % NaOH was diluted in 647.5 g of water. The solution was stirred until it was clear. 84.8 g of 27% Al$_2$(SO$_4$)$_3$ solution was added slowly to the hydroxide solution. 6.7 g of zeolite beta seeds was added to the solution. The solution was mixed for 5-10 minutes. 177.0 g of a precipitated silica (Ultrasil PM modified silica, obtainable from Evonik) was slowly added. 351.2 g of 50 wt. % TEA-Br was added to form a gel. The gel was mixed thoroughly prior to charging to a stirred autoclave, and stirred at 250 rpm at 140° C. for 120 hours. The nominal gel molar composition parameters were as follows:

SiO$_2$/Al$_2$O$_3$=40.7

(Na) alkali/SiO$_2$=0.338

SDA/SiO$_2$=0.305

TEA/Na=1.11

OH$^-$/SiO$_2$=0.338

H$_2$O/SiO$_2$=18.95

Figure 6:
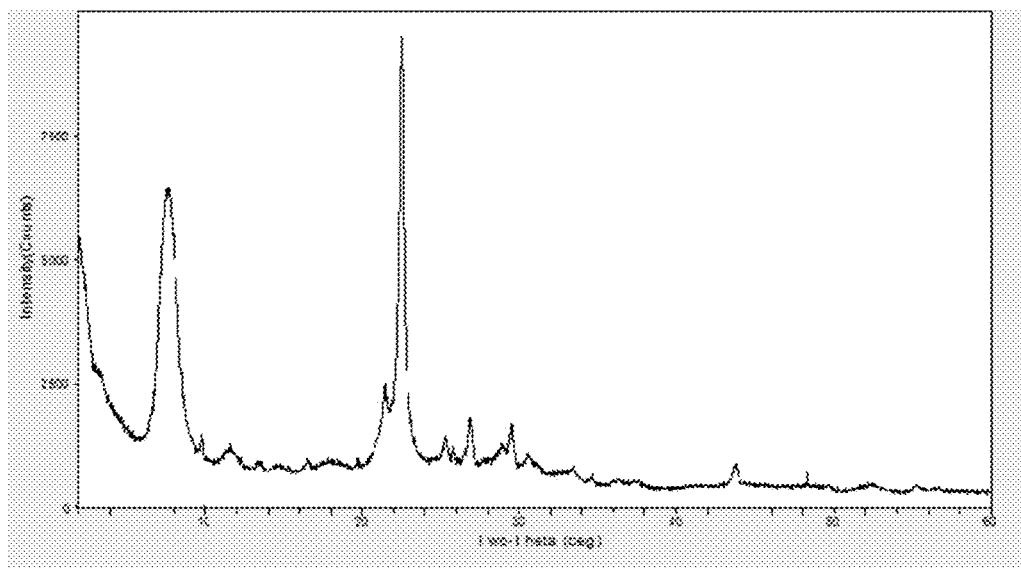
FIG. 6 is the X-ray diffraction pattern for Example 10.

The XRD pattern, as shown in FIG. 6, indicates that the product that was isolated from the reaction mixture was a mixture of beta and mordenite where the amount of beta in the product was approximately 92%. After pre-calcination, ammonium ion exchange, and calcination at 550° C. the collidine uptake was 575 μmoles/g.

Example 11: Precipitated Silica as Silica Source, TEA-OH and TEA-BR as SDA 54.1 g of 50 wt. % NaOH was added to 646.5 g of water to form a NaOH solution. 89.3 g of 35 wt. % TEA-OH (SDA) was added to the NaOH solution. While agitating the NaOH solution, 85.2 g of 47% Al$_2$(SO$_4$)$_3$ was added. 7.4 g of zeolite beta seeds was added. 178.0 g of a precipitated silica (Ultrasil PM modified silica, obtainable from Evonik) was slowly added to the solution. 267.6 g of 50% TEA-Br (SDA) was added and mixed for 30 minutes prior to charging the gel to the autoclave which was stirred at 250 rpm at 140° C. for 120 hours. The nominal gel molar composition parameters were as follows:

SiO$_2$/Al$_2$O$_3$=40.7

(Na) alkali/SiO$_2$=0.12

SDA/SiO$_2$=0.31

OH$^-$/SiO$_2$=0.20

H$_2$O/SiO$_2$=18.51

Figure 7:
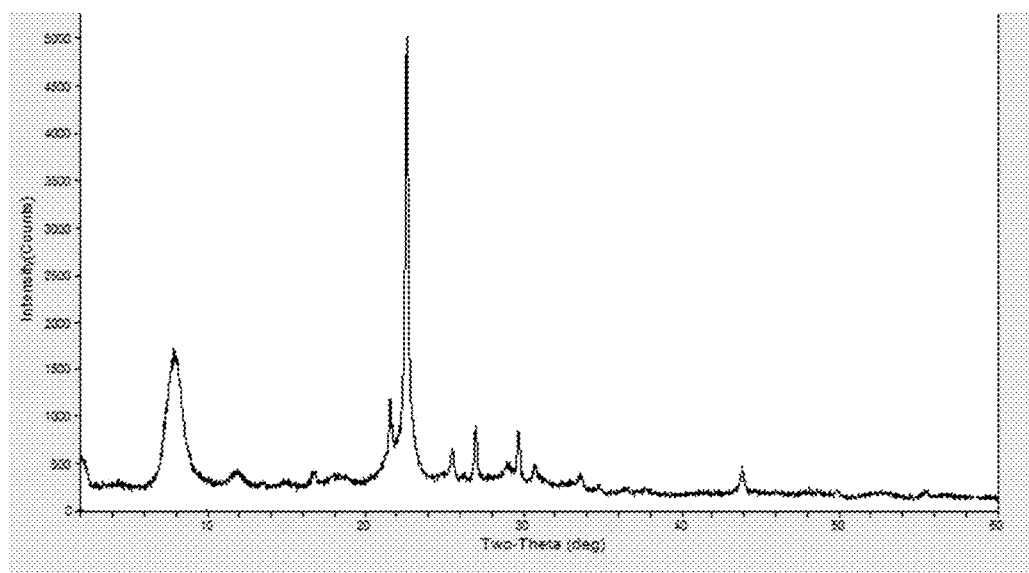
FIG. 7 is the X-ray diffraction pattern for Example 11.

The XRD pattern, as shown in FIG. 7, indicates that the product that was isolated from the autoclave was zeolite beta with no mordenite impurities where the amount of zeolite beta in the product was approximately 100%. After pre-calcination, ammonium ion exchange, and calcination at 550° C. the collidine uptake is approximately 700 μmoles/g.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The invention claimed is:

1. A process for producing a mono-alkylated aromatic compound comprising the steps of:
(a) providing a guard bed having a guard bed catalyst disposed therein, said guard bed catalyst comprises a first catalyst composition comprising a first zeolite having a BEA* framework type and a second zeolite having a MOR framework type and a mesopore surface area of greater than 30 m$^2$/g as measured by BET that is selected from the group consisting of EMM-34, UZM-14, and a combination thereof;
(b) supplying at least a portion of an untreated feed stream to said guard bed, said untreated feed stream comprising an alkylatable aromatic compound and undesirable impurities, wherein said impurities comprise at least one compound having at least one of the following elements: nitrogen, halogens, oxygen, sulfur, arsenic, selenium, tellurium, phosphorus, and Group 1 through Group 12 metals;
(c) contacting said portion of said untreated feed stream of step (b) with said guard bed. catalyst to remove at least a portion of said impurities and produce a treated feed stream having a reduced amount of impurities; and
(d) contacting at least a portion of said treated feed stream of step (c) and an alkylating agent stream with an alkylation catalyst which is the same as said guard bed catalyst under suitable at least partially liquid phase reaction conditions to alkylate at least a portion of said alkylatable aromatic compound with said alkylating agent stream to produce an effluent stream comprising said mono-alkylated aromatic compound and poly-alkylated aromatic compounds.

2. The process of claim 1, wherein step (b) further includes supplying an alkylating agent stream to said guard bed.

3. The process of claim 2, wherein step (c) further includes contacting said alkylating agent stream with said alkylatable aromatic compound in the presence of said guard bed catalyst to produce additional said mono-alkylated aromatic compound.

4. The process of claim 3, wherein said alkylation catalyst comprises an acidic aluminosilicate.

5. The process of claim 4, further comprising the step of:
(e) separating said effluent stream of step (d) to recover a mono-alkylated aromatic compound stream and a poly-alkylated aromatic compounds stream.

6. The process of claim 5, further comprising the step of:
(f) contacting said poly-alkylated aromatic compound stream and another portion of said untreated feed stream of step (b) with a transalkylation catalyst under suitable at least partially liquid phase transalkylation conditions to transalkylate said poly-alkylated aromatic compound stream with said alkylatable aromatic compound and produce additional said mono-alkylated aromatic compound.

7. The process of claim 6, wherein prior to step (f) said another portion of said untreated feed stream is first contacted with a guard bed catalyst to remove at least a portion of said impurities, said guard bed catalyst comprises the first catalyst composition.

8. The process of claim 6, wherein said transalkylation catalyst is a large pore molecular sieve having a constraint index of less than 2 or a MCM-22 family material.

9. The process of claim 8, wherein said large pore molecular sieve is selected from the group consisting of zeolite beta, faujasite, zeolite Y, Ultrastable (USY), Dealuminized Y (Deal Y), Rare Earth Y(REY), Ultrahydrophobic Y (UHP-Y), mordenite, TEA-mordenite, EMM-34, ZSM-2, ZSM-3, ZSM-4, ZSM-14, ZSM-18, ZSM-20, ECR-4, ECR-17, ECR-32, ECR-35 and combinations thereof.

10. The process of claim 1, wherein said alkylatable aromatic compound is benzene, said mono-alkylated aromatic compound is ethylbenzene and said poly-alkylated aromatic compound is poly-ethylbenzene.

11. The process of claim 1, wherein said alkylatable aromatic compound is benzene, said mono-alkylated aromatic compound is cumene and said poly-alkylated aromatic compound is poly-isopropylbenzene.

12. The process of claim 1, wherein said second zeolite is UZM-14.

13. A process for producing a mono-alkylated aromatic compound comprising the steps of:
(a) providing a guard bed having a guard bed catalyst disposed therein, said guard bed catalyst comprises a first catalyst composition comprising a first zeolite having a BEA* framework type and a second zeolite having a MOR framework type and a mesopore surface area of greater than 30 m$^2$/g as measured by BET that is EMM-34;
(b) supplying at least a portion of an untreated feed stream to said guard bed, said untreated feed stream comprising an alkylatable aromatic compound and undesirable impurities, wherein said impurities comprise at least one compound having at least one of the following elements: nitrogen, halogens, oxygen, sulfur, arsenic, selenium, tellurium, phosphorus, and Group 1 through Group 12 metals;
(c) contacting said portion of said untreated feed stream of step (b) with said guard bed. catalyst to remove at least a portion of said impurities and produce a treated feed stream having a reduced amount of impurities; and
(d) contacting at least a portion of said treated feed stream of step (c) and an alkylating agent stream with an alkylation catalyst which is the same or different from said guard bed catalyst under suitable at least partially liquid phase reaction conditions to alkylate at least a portion of said alkylatable aromatic compound with said alkylating agent stream to produce an effluent stream comprising said mono-alkylated aromatic compound and poly-alkylated aromatic compounds.

14. The process of claim 13, wherein step (b) further includes supplying an alkylating agent stream to said guard bed, and wherein step (c) further includes contacting said alkylating agent stream with said alkylatable aromatic compound in the presence of said guard bed catalyst to produce additional said mono-alkylated aromatic compound.

15. The process of claim 14, wherein said alkylation catalyst comprises an acidic aluminosilicate.

16. The process of claim 15, wherein said acidic aluminosilicate is any one of a MCM-22 family molecular sieve, faujasite, mordenite, zeolite beta, or combinations of two or more thereof.

17. The process of claim 15, wherein said acidic aluminosilicate is said MCM-22 family molecular sieve, and wherein said MCM-22 family molecular sieve is any one of MCM-22, PSH-3, SSZ-25, MCM-36, MCM-49, MCM-56, ERB-1, EMM-10, EMM-10-P, EMM-12, EMM-13, UZM-8, UZM-8HS, UZM-37, ITQ-1, ITQ-2, ITQ-30, MIT-1, or combinations of two or more thereof.

18. The process of claim 17, further comprising the step of:
(e) separating said effluent stream of step (d) to recover a mono-alkylated aromatic compound stream and a poly-alkylated aromatic compounds stream.

19. The process of claim 18, further comprising the step of:
(f) contacting said poly-alkylated aromatic compound stream and another portion of said untreated feed stream of step (b) with a transalkylation catalyst under suitable at least partially liquid phase transalkylation conditions to transalkylate said poly-alkylated aromatic compound stream with said alkylatable aromatic compound and produce additional said mono-alkylated aromatic compound.

20. The process of claim 19, wherein prior to step (f) said another portion of said untreated feed stream is first contacted with a guard bed catalyst to remove at least a portion of said impurities, said guard bed catalyst comprises the first catalyst composition.

21. The process of claim 19, wherein said transalkylation catalyst is a large pore molecular sieve having a constraint index of less than 2 or a MCM-22 family material.

22. The process of claim 21, wherein said large pore molecular sieve is selected from the group of consisting of zeolite beta, faujasite, zeolite Y, Ultrastable Y (USY), Dealuminized Y (Deal Y), Rare Earth Y(REY), Ultrahydrophobic Y (UHP-Y), mordenite, TEA-mordenite, EMM-34, ZSM-2, ZSM-3, ZSM-4, ZSM-14, ZSM-18, ZSM-20, ECR-4, ECR-17, ECR-32, ECR-35, and combinations thereof.

23. The process of claim 13, wherein said alkylatable aromatic compound is benzene, said mono-alkylated aromatic compound is ethylbenzene and said poly-alkylated aromatic compound is poly-ethylbenzene.

24. The process of claim 13, wherein said alkylatable aromatic compound is benzene, said mono-alkylated aromatic compound is cumene and said poly-alkylated aromatic compound is poly-isopropylbenzene.

* * * * *